US012369890B2

(12) United States Patent
Honjo et al.

(10) Patent No.: US 12,369,890 B2
(45) Date of Patent: Jul. 29, 2025

(54) ULTRASOUND DIAGNOSTIC APPARATUS, ANALYSIS DEVICE, AND ANALYSIS METHOD (71) Applicant: CANON MEDICAL SYSTEMS CORPORATION, Otawara (JP)

(72) Inventors: Yasunori Honjo, Utsunomiya (JP); Tomohisa Imamura, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 184 days.

(21) Appl. No.: 18/298,413

(22) Filed: Apr. 11, 2023

(65) Prior Publication Data

US 2023/0329677 A1    Oct. 19, 2023

(30) Foreign Application Priority Data

Apr. 13, 2022    (JP) .................................. 2022-066441

(51) Int. Cl.
  *A61B 8/00*    (2006.01)
(52) U.S. Cl.
  CPC ............ *A61B 8/485* (2013.01); *A61B 8/5276* (2013.01); *A61B 8/543* (2013.01)
(58) Field of Classification Search
  CPC ........ A61B 8/485; A61B 8/5276; A61B 8/543
  See application file for complete search history.

(56) References Cited

U.S. PATENT DOCUMENTS

| 2015/0182122 | A1* | 7/2015 | Bamber | G01S 7/52022 |
| | | | | 600/407 |
| 2016/0095582 | A1 | 4/2016 | Iwama et al. | |
| 2019/0261949 | A1* | 8/2019 | Labyed | G06T 7/0012 |
| 2020/0060654 | A1* | 2/2020 | Nguyen | G01S 7/52042 |
| 2020/0069294 | A1 | 3/2020 | Sato | A61B 8/0891 |
| 2022/0211352 | A1* | 7/2022 | Kim | A61B 8/06 |
| 2022/0413136 | A1* | 12/2022 | Tanaka | G01S 15/8979 |

FOREIGN PATENT DOCUMENTS

JP    2016-73452 A    5/2016

* cited by examiner

*Primary Examiner* — Sean A Frith
(74) *Attorney, Agent, or Firm* — Oblon, McClelland, Maier & Neustadt, L.L.P.

(57) ABSTRACT

An ultrasound diagnostic apparatus according to an embodiment includes processing circuitry. The processing circuitry calculates, based on first ultrasound information relating to a displacement over time of an organ that makes a periodic movement, a function relating to a clutter component originating from the organ, and calculates, based on the function and second ultrasound information relating to a displacement over time of the organ after pressure is applied to the organ, a shear wave that propagates through the organ by the applied pressure.

12 Claims, 6 Drawing Sheets

ULTRASOUND DIAGNOSTIC APPARATUS, ANALYSIS DEVICE, AND ANALYSIS METHOD

CROSS-REFERENCE TO RELATED APPLICATIONS

This application is based upon and claims the benefit of priority from Japanese Patent Application No. 2022-066441, filed on Apr. 13, 2022; the entire contents of which are incorporated herein by reference.

FIELD

Embodiments described herein relate generally to an ultrasound diagnostic apparatus, an analysis device, and an analysis method.

BACKGROUND

Conventionally, a technique called shear wave elastography (SWE) to measure a hardness distribution of an organ of a subject by using ultrasonic waves has conventionally been available. In SWE, an ultrasound diagnostic apparatus applies pressure to an organ using ultrasonic waves to generate shear waves within the organ. The ultrasound diagnostic apparatus measures a displacement caused by the shear waves propagating through the organ, to estimate the hardness of various points in the organ.

However, organs that make a periodic movement, such as heart, are displaced by their own movement, and it is, accordingly, difficult to measure the displacement in shear waves caused by applied pressure.

DETAILED DESCRIPTION

Hereinafter, an embodiment of an ultrasound diagnostic apparatus, an analysis device, and an analysis method will be explained with reference to the drawings. In the embodiment below, components assigned with common reference signs perform similar operations, and duplicated explanation will be omitted as appropriate.

Figure 1:
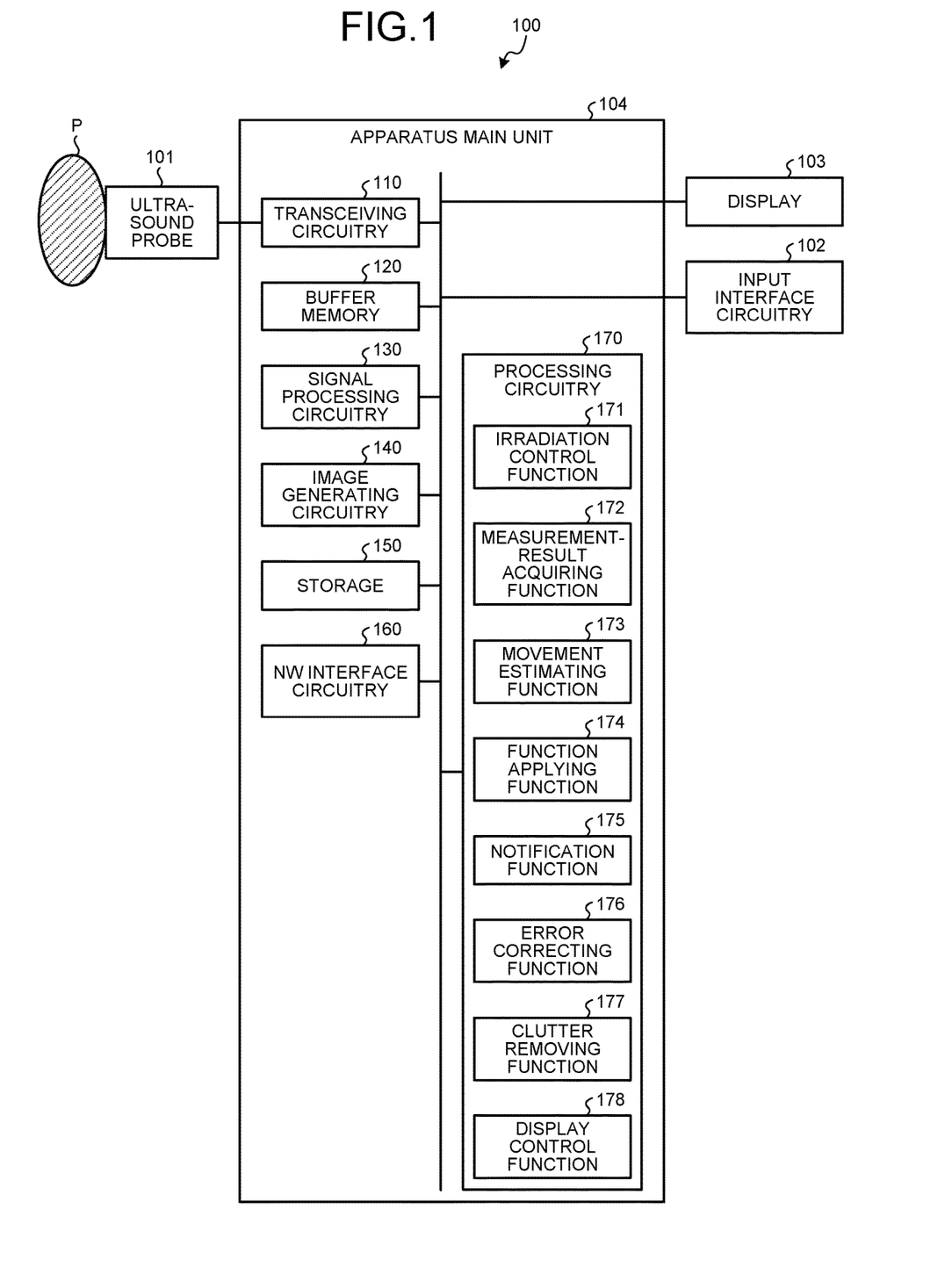
FIG. 1 is a block diagram illustrating a configuration example of an ultrasound diagnostic apparatus according to the present embodiment.

FIG. 1 is a block diagram illustrating a configuration example of an ultrasound diagnostic apparatus 100 according to the present embodiment. As illustrated in FIG. 1, the ultrasound diagnostic apparatus 100 includes an ultrasound probe 101, input interface circuitry 102, a display 103, and an apparatus main unit 104. The ultrasound probe 101, the input interface circuitry 102, and the display 103 are connected to the apparatus main unit 104 in a communication-enabled manner.

The ultrasound probe 101 includes plural piezoelectric transducers, and these piezoelectric transducers generate ultrasonic waves based on a driving signal supplied from a transceiving circuit included in the apparatus main unit 104. Moreover, the ultrasound probe 101 receives a reflection wave from the subject P and converts it into an electrical signal. For example, in SWE, the ultrasound probe 101 irradiates pulsed ultrasonic waves, and receives reflection waves. The ultrasound probe 101 is detachably connected to the apparatus main unit 104.

When ultrasonic waves are transmitted to the subject P from the ultrasound probe 101, the transmitted ultrasonic waves are reflected successively on a discontinuous surface of an acoustic impedance in a body tissue of the subject P, and are received by the piezoelectric transducers included in the ultrasound probe 101 as reflection wave signals. An amplitude of a received reflection wave signal is dependent on a difference in the acoustic impedance on the discontinuous surface on which the ultrasonic wave is reflected. A reflection wave signal obtained when a transmitted ultrasonic wave pulse is reflected on moving blood flow or on a surface of a heart wall is subject to frequency shift depending on a velocity component with respect to a direction of transmission of an ultrasonic wave of a moving body due to the Doppler effect.

Forms of the ultrasound probe 101 are not particularly limited, and any form of ultrasound probe may be used therefor. For example, the ultrasound probe 101 may be a 1D-array probe that scans the subject P in two dimensions. Moreover, the ultrasound probe 101 may be a mechanical 4D probe or a 2D-array probe that scans the subject P in three dimensions.

The input interface circuitry 102 accepts an input operation of various kinds of instructions and information from an operator. Specifically, the input interface circuitry 102 converts an input operation accepted from an operator into an electrical signal, to output to a processing circuitry 170 of the apparatus main unit 104. For example, the input interface circuitry 102 is implemented by a trackball, a switch button, a mouse, a keyboard, a touch pad with which input operation is performed by touching an operating surface, a touch screen in which a display screen and a touch pad are integrated, a non-contact input circuit using an optical sensor, a sound input circuit, and the like. The input interface circuitry 102 is not limited to those including a physical operating part, such as a mouse and a keyboard. For example, a processing circuit of an electrical signal that receives an electrical signal corresponding to an input operation from an external input device provided separated from the apparatus, and outputs this electrical signal to the control circuit is also included in examples of the input interface circuitry 102.

The display 103 displays various kinds of information and images. Specifically, the display 103 converts data of information and image transmitted from the processing circuitry 170 into an electrical signal for display, and outputs it for display. For example, the display 103 is implemented by a liquid crystal monitor, a cathode ray tube (CRT) monitor, a touch panel, and the like. As an output device included in the ultrasound diagnostic apparatus 100, not limited to the display 103, for example, a speaker may be included. For example, a speaker outputs predetermined sounds, such as a beep tone, to notify of a processing state of the apparatus main unit 104 to the operator.

The apparatus main unit 104 is a device that generates an ultrasound image based on a reflection wave signal received by the ultrasound probe 101. For example, the apparatus main unit 104 generates a two-dimensional ultrasound image based on a two-dimensional reflection wave data received by the ultrasound probe 101. Moreover, the apparatus main unit 104 generates a three-dimensional ultrasound image based on a three-dimensional reflection wave data received by the ultrasound probe 101.

The apparatus main unit 104 includes, as illustrated in FIG. 1, transceiving circuitry 110, a buffer memory 120, signal processing circuitry 130, image generating circuitry 140, a storage 150, network (NW) interface circuitry 160, and processing circuitry 170. The transceiving circuitry 110, the buffer memory 120, the signal processing circuitry 130, the image generating circuitry 140, the storage 150, the NW interface circuitry 160, and the processing circuitry 170 are connected to one another in a communication-enabled manner.

To the apparatus main unit 104, an electrocardiogram that records electrical potentials of cardiac muscle cells along with the heartbeat of the subject P that is scanned by ultrasonic waves may be connected. The electrocardiogram generates an electrocardiographic waveform that represents the heartbeat of the heart of the subject P.

The transceiving circuitry 110 includes a pulse generator, a transmission delay unit, a pulser, and the like, and supplies a driving signal to the ultrasound probe 101. The pulse generator repeatedly generates a rate pulse to form a transmission ultrasonic wave at a predetermined rate frequency. Moreover, the transmission delay unit converges ultrasonic waves generated by the ultrasound probe 101 into a beam shape, and gives a delay for each piezoelectric transducer necessary to determine a transmission directivity, to each rate pulse generated by the pulse generator. Moreover, the pulser applies a driving signal (driving pulse) to the ultrasound probe 101 at a timing based on the rate pulse. That is, the transmission delay unit varies the delay to be applied to each rate pulse, and thereby adjusts the transmission direction of an ultrasonic wave to be transmitted from a transducer surface arbitrarily.

Furthermore, the transceiving circuitry 110 includes a preamplifier, an analog-to-digital (A/D) converter, an orthogonal detection circuit, and the like, and generates reflection wave data by performing various kinds of processing with respect to a reflection wave signal received by the ultrasound probe 101. The transceiving circuitry 110 stores the generated reflection wave data in the buffer memory 120.

The preamplifier performs gain adjustment (gain correction) by amplifying the reflection wave signal per channel. The A/D converter A/D converts the reflection wave signal subjected to the gain correction, and thereby converts the reflection wave signal subjected to the gain correction into a digital signal. The orthogonal detection circuit converts the reflection wave signal subjected to the A/D conversion into an in-phase signal (I signal) and a quadrature-phase signal (Q signal) within a baseband bandwidth.

The orthogonal detection circuit outputs the I-signal and the Q-signal as the reflection wave data. Hereinafter, when collectively referring to the I-signal and the Q-signal, they are referred to as IQ signal. Moreover, because the IQ signal is digital data subjected to the A/D conversion, it is also referred to as IQ data.

The buffer memory 120 is implemented, for example, by a semiconductor memory, such as a random access memory (RAM) and a flash memory. The buffer memory 120 stores reflection wave data output from the transceiving circuitry 110.

The signal processing circuitry 130 performs logarithmic amplification, envelope detection processing, and the like on the reflection wave data acquired from the buffer memory 120, to generate data (B-mode data) representing signal strength with brightness. Moreover, the signal processing circuitry 130 performs frequency analysis on velocity information in the reflection wave data acquired from the buffer memory 120, and extracts echo components of blood flow, a tissue, and a contrast agent by the Doppler effect, to generate data (Doppler data) obtained by extracting moving object information, such as velocity, distribution, and power, at multiple points. The moving object is, for example, blood flow, a tissue of an organ that moves periodically, such as a heart wall, and a contrast agent.

Moreover, the signal processing circuitry 130 is capable of processing both two-dimensional reflection wave data and three-dimensional reflection wave data. That is, the signal processing circuitry 130 generates two-dimensional B-mode data from two-dimensional reflection wave data, and generates three-dimensional B-mode data from three-dimensional reflection wave data. Furthermore, the signal processing circuitry 130 generates two-dimensional Doppler data from two-dimensional reflection wave data, and generates three-dimensional Doppler data from three-dimensional reflection data.

The image generating circuitry 140 generates a ultrasound image from data generated by the signal processing circuitry 130. For example, the image generating circuitry 140 generates two-dimensional B-mode data in which the strength of the reflection wave is represented by brightness from the two-dimensional B-mode data generated by the signal processing circuitry 130.

Moreover, the image generating circuitry 140 generates Doppler image data that shows the moving object information from the Doppler data generated by the signal processing circuitry 130. The Doppler image data is velocity image data, dispersion image data, power image data, or image data in which these are combined.

Furthermore, for example, the image generating circuitry 140 can generate M-mode image also from chronological data of the B-mode data on one scan line generated by the signal processing circuitry 130. Moreover, the image generating circuitry 140 can generate a Doppler waveform in which velocity information of blood flow or a tissue is chronologically plotted, from the Doppler data generated by the signal processing circuitry 130.

Generally, the image generating circuitry 140 converts (scan converts) a scan line signal sequence of ultrasound scanning into a scan line signal sequence of a video format represented by television and the like, to generate an ultrasound image for display. Specifically, the image generating circuitry 140 generates an ultrasound image for display by performing coordinate conversion according to a scanning form of ultrasonic waves by the ultrasound probe 101. Moreover, other than scan conversion, the image generating circuitry 140 performs, for example, image processing (smoothing processing) to regenerate a mean luminance image by using plural image frames subjected to the scan conversion, image processing (edge enhancement processing) using a differential filter in an image, and the like as various kinds of image processing. Furthermore, the image generating circuitry 140 superimposes character information of various parameters, scales, body marks, and the like on the ultrasound image data.

That is, the B-mode data and the Doppler data are data before scan conversion processing, and data generated by the image generating circuitry 140 is image data for display after scan conversion processing. Hereinafter, data before scan conversion processing (B-mode data and Doppler data) is also referred to as "RAW" data.

The image generating circuitry 140 generates a two-dimensional B-mode image and a two-dimensional Doppler image from two-dimensional B-mode data and two-dimensional Doppler data, which are RAW data. Moreover, the image generating circuitry 140 can also generate a superimposition image in which, for example, a color Doppler image is superimposed on a two-dimensional B-mode image.

The storage 150 stores various kinds of data. For example, the storage 150 stores various kinds of data, such as control programs to perform ultrasound transmission and reception, image processing, and display processing, diagnostic information (for example, patient ID, doctor's findings, and the like), diagnostic protocols, and various kinds of body marks. For example, the storage 150 is implemented by a semiconductor memory device, such as a RAM and a flash memory, a hard disk drive (HDD), an optical disk, and the like.

Furthermore, data stored in the storage 150 can be transferred to an external device through the NW interface circuitry 160. The external device is, for example, a personal computer (PC) that is used by a doctor performing diagnostic imaging, a tablet terminal, an image storage device to store images, a printer, and the like.

The NW interface circuitry 160 controls communications between the apparatus main unit 104 and an external device. Specifically, the NW interface circuitry 160 receives various kinds of information from the external device, and outputs the received information to the processing circuitry 170. For example, the NW interface circuitry 160 is implemented by a network card, a network adaptor, a network interface controller (NIC), and the like.

The processing circuitry 170 controls the entire processing of the ultrasound diagnostic apparatus 100. Specifically, the processing circuitry 170 controls processing of the transceiving circuitry 110, the signal processing circuitry 130, and the image generating circuitry 140 based on various kinds of setting requests input by an operator through the input interface circuitry 102, and various kinds of control programs and data retrieved from the storage 150. Moreover, the processing circuitry 170 controls display of ultrasound images.

Furthermore, the processing circuitry 170 performs an irradiation control function 171, a measurement-result acquiring function 172, a movement estimating function 173, a function applying function 174, a notification function 175, an error correcting function 176, a clutter removing function 177, and a display control function 178. For example, respective processing functions of the irradiation control function 171, the measurement-result acquiring function 172, the movement estimating function 173, the function applying function 174, the notification function 175, the error correcting function 176, the clutter removing function 177, and the display control function 178 are stored in the storage 150 in a form of computer-executable program. The processing circuitry 170 is a processor. For example, the processing circuitry 170 implements the functions corresponding to the respective programs by reading out and executing the programs from the storage 150. In other words, the processing circuitry 170 that has read out the respective programs is to have the respective functions indicated in the processing circuitry 170 in FIG. 1. Although it has been explained that the processing functions performed by the irradiation control function 171, the measurement-result acquiring function 172, the movement estimating function 173, the function applying function 174, the notification function 175, the error correcting function 176, the clutter removing function 177, and the display control function 178 are implemented by a single unit of processor in FIG. 1, the processing circuitry 170 may be configured by combining plural independent processors, and may implement the functions with the respective processor executing the respective programs. Moreover, although it has been explained that a single unit of the storage 150 stores programs corresponding to the respective processing functions in FIG. 1, plural units of storage circuits may be arranged in a distributed manner, and the processing circuitry 170 may be configured to read out a corresponding program from an individual storage circuit.

The term "processor" used in the above explanation signifies a circuit, such as a central processing unit (CPU), a graphical processing unit (GPU), an application specific integrated circuit (ASIC), a programmable logic device (for example, simple programmable logic device (SPLD), complex programmable logic device (CPLD)), and a field programmable gate array (FPGA). The processor implements a function by reading out and executing a program stored in the storage 150. Instead of storing a program in the storage 150, it may be configured to directly install a program in a circuit of the processor. In this case, the processor reads out and executes the program installed in the circuit, to implement the function.

The ultrasound diagnostic apparatus 100 performs SWE to measure a hardness distribution of an organ of a subject P. The ultrasound diagnostic apparatus 100 performs SWE with respect to an organ that makes a periodic movement, such as the heart. Moreover, the organ is not limited to the heart, but may be any organ that makes a periodic movement. For example, the organ may be a pulsating circulatory organ, a pulsating blood vessel, or any other organs.

The ultrasound diagnostic apparatus 100 applies pressure to an organ subject to measurement by irradiating pulsed ultrasonic waves in SWE. Moreover, the ultrasound diagnostic apparatus 100 measures a shear wave that is caused by application of pressure, and that propagates through the organ. An amount of movement of each point in the organ when pressure is applied, that is, a displacement, differs between a soft part and a hard part. The ultrasound diagnostic apparatus 100 estimates the hardness of respective parts of the organ by measuring a shear wave. The ultrasound diagnostic apparatus 100 visualizes and displays a hardness estimation result in an image. Thus, medical professionals can detect a lesion.

However, in an organ that makes a periodic movement, such as the heart, a displacement of the organ itself occurs. That is, the displacement acquired from an organ that makes a periodic movement includes a displacement of the organ itself and a displacement due to a shear wave caused by applying pressure. Therefore, the ultrasound diagnostic apparatus 100 removes a clutter component, such as a displacement of the organ itself, out of the displacement acquired from the organ subject to measurement. Thus, the ultrasound diagnostic apparatus 100 acquires a displacement due to a shear wave that propagates through the organ to which pressure is applied.

Figure 2:
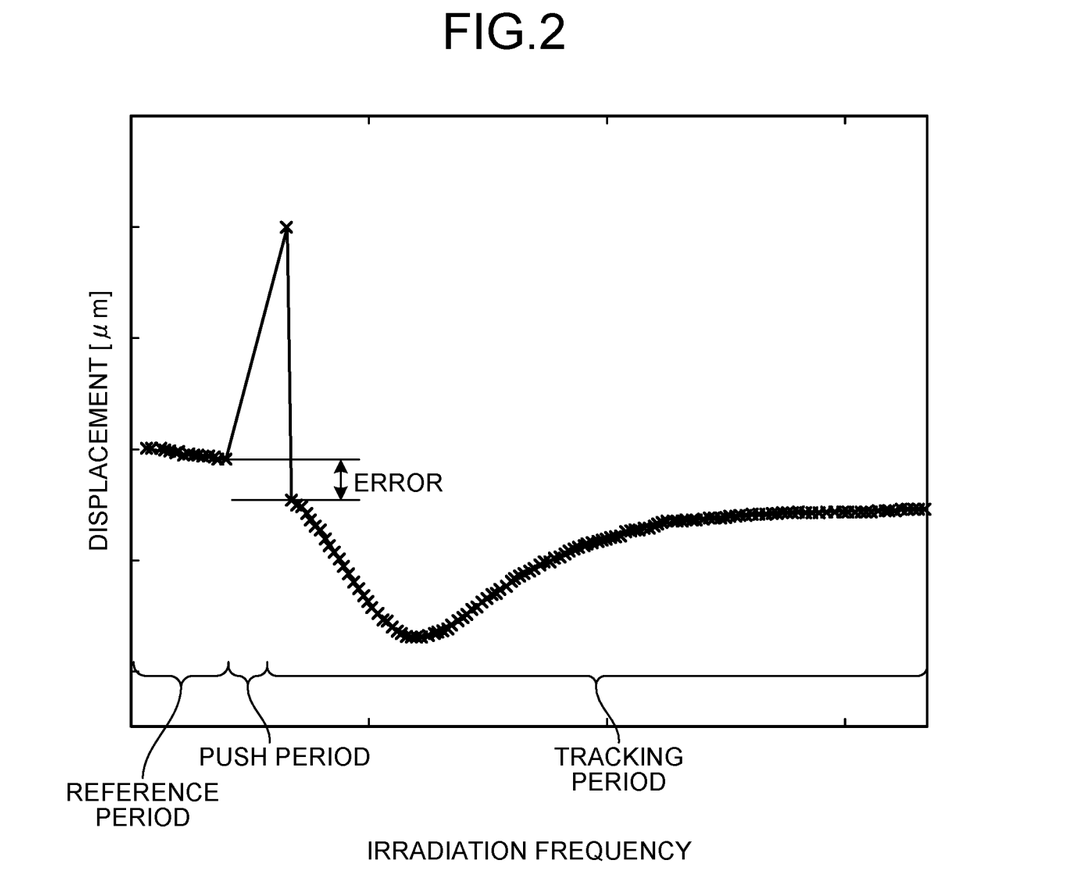
FIG. 2 is a graph showing an example of a measurement result acquired by the ultrasound diagnostic apparatus.

FIG. 2 is a graph showing an example of a measurement result obtained by the ultrasound diagnostic apparatus 100. In the graph in FIG. 2, a vertical axis represents a displacement, which is an amount of movement of an organ of the subject P, and a horizontal axis represents the frequency of irradiation of an ultrasonic wave. That is, the graph in FIG. 2 is a graph in which Doppler data of an ultrasonic wave irradiated to an organ of the subject P is plotted.

In SWE, the ultrasound diagnostic apparatus 100 irradiates a pulsed ultrasonic wave in a reference period, in a push period, and in a tracking period. The reference period is a period in which a periodic movement of an organ subject to measurement are measured. The ultrasound diagnostic apparatus 100 irradiates a reference pulse in the reference period, and receives a reflection wave of the reference pulse. Thus, the ultrasound diagnostic apparatus 100 acquires a displacement caused by the periodic movement of the organ. The reference pulse is a pulsed ultrasonic wave that is irradiated in the reference period.

The push period is a period in which pressure is applied to an organ subject to measurement. The ultrasound diagnostic apparatus 100 applies pressure to an organ by irradiating a push pulse in the push period. The push pulse is a pulsed ultrasonic wave to be irradiated in the push period, and is an ultrasonic wave that pushes the organ subject to measurement. The ultrasound diagnostic apparatus 100 does not acquire a reflection wave during the push period.

The tracking period is a period in which a displacement caused by a shear wave that propagates through an organ by applying pressure to the organ is measured. The ultrasound diagnostic apparatus 100 irradiates the tracking pulse in the tracking period, and receives a reflection wave of the reference pulse. Thus, the ultrasound diagnostic apparatus 100 acquires a displacement caused by shear waves that propagate through the organ.

In the push period in which a push pulse is irradiated shown in FIG. 2, the ultrasound diagnostic apparatus 100 does not receive a reflection wave. Therefore, continuity is lost in an interval between the reference period and the tracking period, and an error occurs. In addition, as shown in FIG. 2, the organ subject to measurement undergoes a displacement of the organ itself. Accordingly, a component that interferes with measurement of a shear wave that propagates through the organ is included in the Doppler data.

Therefore, in the reference period, the ultrasound diagnostic apparatus 100 repeatedly irradiates the reference pulse during a period in which the organ that makes a periodic movement moves at least for one cycle. The ultrasound diagnostic apparatus 100 generates Doppler data from reflection wave data of the reference pulse repeatedly irradiated during the reference period. The ultrasound diagnostic apparatus 100 generates first displacement information in which a displacement over time of an organ that makes a periodic movement is recorded based on the Doppler data. Moreover, the ultrasound diagnostic apparatus 100 calculates a function representing the displacement over time of the organ that makes periodic movement based on the first displacement information. The ultrasound diagnostic apparatus 100 interpolates a portion in which the continuity is lost by the push pulse based on the function, removes a displacement of the organ itself, and thereby extracts a displacement caused by a shear wave that propagates through the organ.

Specifically, the ultrasound diagnostic apparatus 100 is implemented by the following functions.

The irradiation control function 171 controls the ultrasound probe 101 to irradiate a pulsed ultrasonic wave in the reference period, the push period, and the tracking period. More specifically, the irradiation control function 171 causes the ultrasound probe 101 to repeatedly irradiate the reference pulse, which is a pulsed ultrasonic wave, each time a predetermined period passes, during the reference period. The irradiation control function 171 controls to repeatedly irradiate the reference pulse to an organ that makes a periodic movement during a period of at least one cycle. That is, the irradiation control function 171 controls to irradiate the reference pulse during a period of one beat or more of an organ such as the heart. Moreover, the irradiation control function 171 can improve robustness as the number of times of beats increases during a period in which the reference pulse is irradiated.

Furthermore, the irradiation control function 171 causes the ultrasound probe 101 to repeatedly irradiate the push pulse, which is a pulsed ultrasonic wave, each time a predetermined period passes, during the push period.

Moreover, the irradiation control function 171 causes the ultrasound probe 101 to repeatedly irradiate the tracking pulse, which is a pulsed ultrasonic wave, each time a predetermined period passes, during the tracking period. When application of pressure to an organ and measurement of a shear wave caused by the applied pressure are repeatedly performed, the irradiation control function 171 repeats the processing, for example, in order of the reference period, the push period, and the tracking period. The irradiation control function 171 repeatedly irradiates a pulsed ultrasonic wave in each period.

Figure 3:
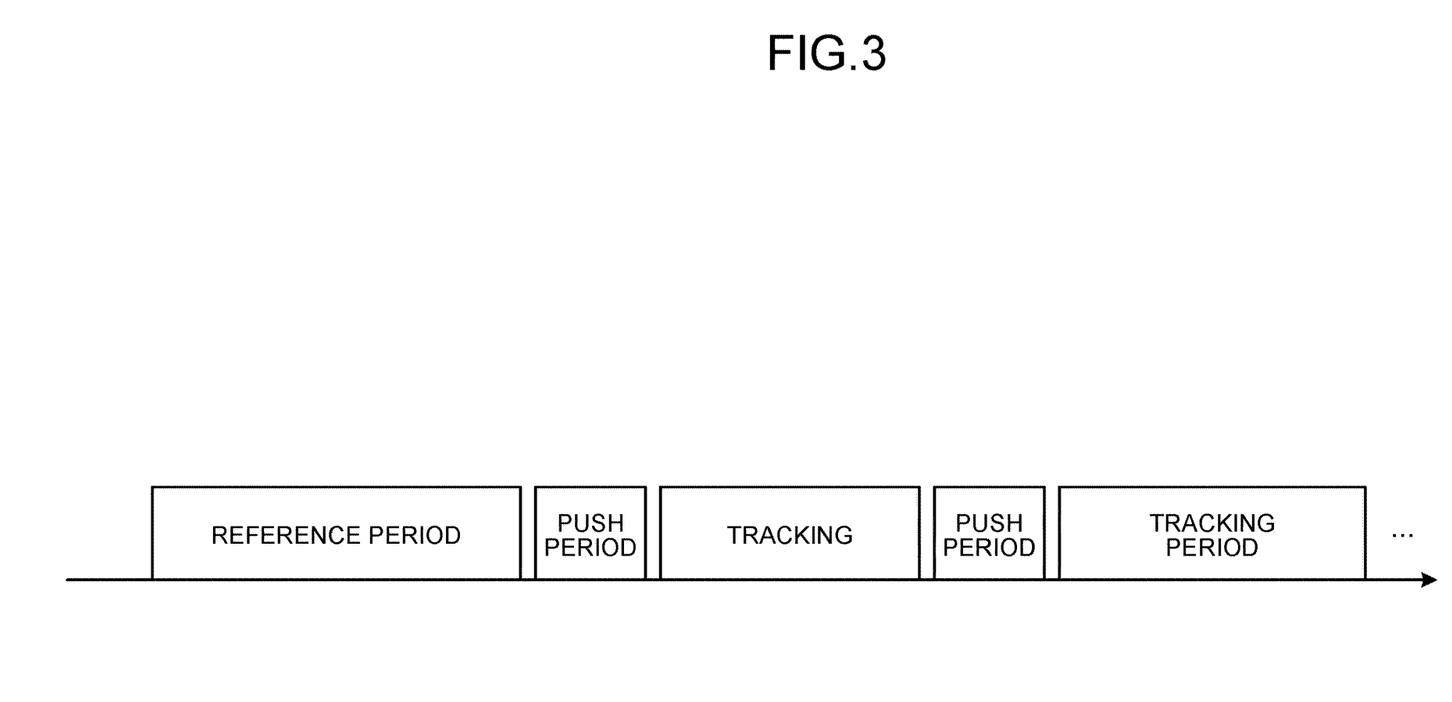
FIG. 3 is a diagram illustrating an example of the order of irradiation of ultrasonic waves by the ultrasound diagnostic apparatus.

The irradiation control function 171 may repeat the push period and the tracking period after the reference period passes. FIG. 3 is a diagram illustrating an example of order of irradiation of an ultrasonic wave by the ultrasound diagnostic apparatus 100. As illustrated in FIG. 3, the irradiation control function 171 controls to irradiate the reference pulse repeatedly in the reference period. Thereafter, the irradiation control function 171 may control to perform repeated irradiation of the push pulse in the push period and repeated irradiation of the tracking pulse in the tracking period alternately. That is, the ultrasound probe 101 performs the repeated irradiation of the push pulse, which is a pulsed ultrasonic wave to apply pressure to an organ and the repeated irradiation of the tracking pulse, which is a pulsed ultrasonic wave to acquire second displacement information alternately after repeatedly irradiating the reference pulse, which is a pulsed ultrasonic wave to acquire the first displacement information. In this case, the irradiation control function 171 can reduce execution time because after the reference period passes, only the push period and the tracking period are repeated.

The measurement-result acquiring function 172 collects measurement results. Reflection wave data of the respective pulsed ultrasonic waves irradiated by the irradiation control function 171 is stored in the buffer memory 120. The signal processing circuitry 130 generates Doppler data from the reflection wave data stored in the buffer memory 120. The measurement-result acquiring function 172 collects the respective Doppler data of the reference pulse repeatedly irradiated during the reference period as the first displacement information in which a displacement over time of an organ that makes a periodic movement is recorded.

Moreover, the measurement-result acquiring function 172 collects the respective Doppler data of the tracking pulse repeatedly irradiated during the tracking period as the second displacement information in which a displacement over time after pressure is applied to the organ.

The movement estimating function 173 estimates a movement of an organ that makes a periodic movement. That is, the movement estimating function 173 calculates a function relating to a clutter component from the organ based on the first displacement information relating to a displacement over time of the organ that makes a periodic movement. The clutter component is an unnecessary component originating from the organ and is, for example, a displacement over time caused by a movement of the organ itself. The movement estimating function 173 is one example of a first calculating unit. The first displacement information is one example of first ultrasound information.

Figure 4:
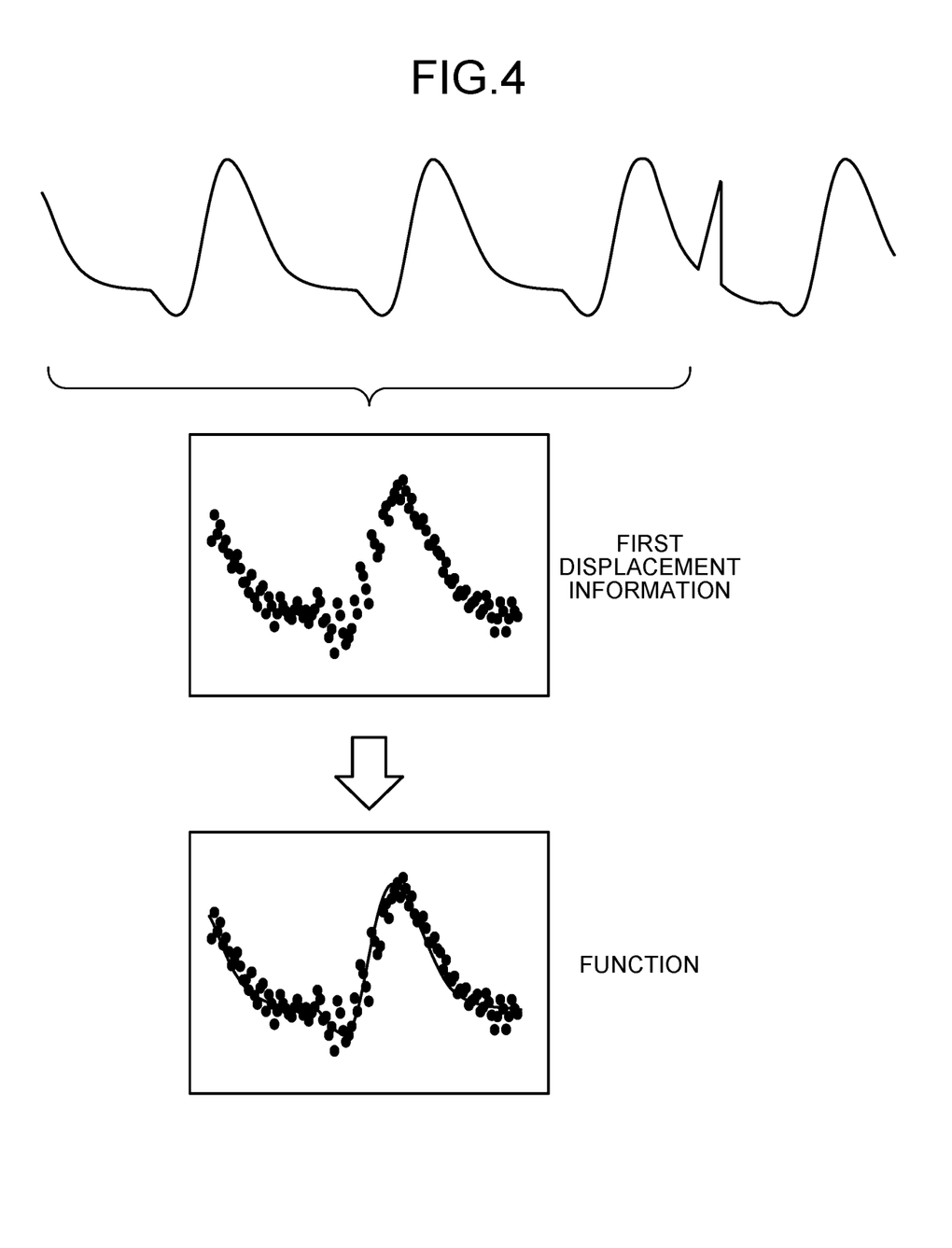
FIG. 4 is a diagram illustrating an example of a calculation method of a function based on first displacement information.

FIG. 4 is a diagram illustrating an example of a calculation method of a function based on the first displacement information. As illustrated in FIG. 4, the movement estimating function 173 calculates a function relating to a clutter component originating from an organ based on the first displacement information in which a displacement over time of the organ of at least one cycle is included. In other words, the movement estimating function 173 calculates a function representing a displacement over time of an organ. For example, the movement estimating function 173 calculates the function representing a displacement over time of an organ by calculating a kernel function for Gaussian process. Not limited thereto, the movement estimating function 173 may perform calculation by polynomial fitting in which parameters of the function are inferred, by the least squares method, or the like.

The function applying function 174 synchronizes a clutter component originating from an organ represented by a function calculated by the movement estimating function 173 and a displacement over time of the organ indicated by the second displacement information. The function applying function 174 is one example of a synchronizing unit. In other words, the function applying function 174 cuts out a range to be a subject to comparison out of functions calculated by the movement estimating function 173.

Figure 5:
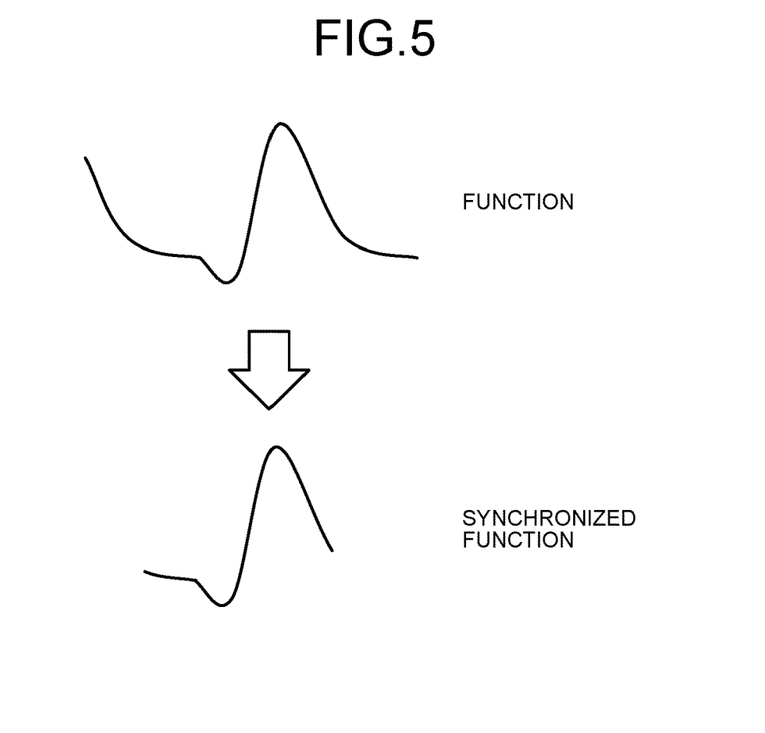
FIG. 5 is an explanatory diagram illustrating an example of synchronization of a displacement of an organ over time represented by a function and a displacement indicated by reflection wave data of a tracking pulse.

FIG. 5 is an explanatory diagram illustrating an example of the synchronization of a displacement over time of an organ represented by a function and a displacement indicated by reflection wave data of the tracking pulse. The ultrasound diagnostic apparatus 100 compares the displacement over time of an organ represented by a function and the displacement indicated by reflection wave data of the tracking pulse. For an organ that makes a periodic movement, the ultrasound diagnostic apparatus 100 cannot obtain a significant result even if a displacement at a point of a 1/4 cycle and a displacement at a point of a 2/4 cycle are compared. Therefore, as illustrated in FIG. 5, the function applying function 174 synchronizes the displacement over time of an organ represented by a function and the displacement indicated by reflection wave data of each tracking pulse to match the displacements subject to comparison.

For example, the function applying function 174 synchronizes a clutter component originating from the organ represented by a function and a displacement over time indicated by the second displacement information based on an electrocardiographic waveform of the organ. Specifically, the function applying function 174 identifies a period in which the reflection wave data of the tracking pulse is received based on an electrocardiographic waveform when the organ subject to measurement is heart. That is, the function applying function 174 determines which period in the electrocardiographic waveform corresponds to the period in which the reflection wave data of the tracking pulse is received. The function applying function 174 cuts out a period corresponding to the identified period out of the displacement over time of the organ represented by a function. Thus, the function applying function 174 synchronizes the clutter component originating from the organ represented by the function and the displacement indicated by the reflection wave data of each tracking pulse.

Alternatively, the function applying function 174 synchronizes a displacement over time represented by a function and a displacement over time indicated by the second displacement information based on a correlation function to calculate a similarity between a clutter component originating from the organ represented by a function and the displacement over time indicated by the second displacement information. The correlation function calculates the similarity between a waveform indicating a displacement over time of an organ represented by a function and a waveform indicating a displacement over time of the organ indicated by the second displacement information, while changing a section of the waveforms. The function applying function 174 extracts a section having the highest similarity to a waveform of the displacement indicated by the reflection wave data of each tracking pulse out of the waveform of the displacement over time of the organ represented by a function. Thus, the function applying function 174 synchronizes the clutter component originating from the organ represented by a function and the displacement indicated by the reflection wave data of each tracking pulse.

While the push pulse is irradiated, the ultrasound diagnostic apparatus 100 does not receive a reflection wave of the push pulse. Therefore, the function applying function 174 cuts out a range corresponding to the period in which the push pulse is irradiated out of the function calculated by the movement estimating function 173, to estimate a displacement in the period in which the push pulse is irradiated. For example, when synchronizing a clutter component originating from an organ represented by a function and a displacement indicated by the reflection wave data of the tracking pulse, the function applying function 174 synchronizes the period in which the push pulse is irradiated first. Thus, the function applying function 174 cuts out a range corresponding to the period in which the push pulse is irradiated. Alternatively, the function applying function 174 cuts out a range corresponding to the period in which the push pulse is irradiated by identifying the period in which the push pulse is irradiated based on an electrocardiographic waveform.

The notification function 175 notifies when the similarity indicating the degree of similarity between a clutter component originating from an organ represented by a function and a displacement over time of the organ indicated by the second displacement information are is lower than threshold. The notification function 175 is one example of a notifying unit. When the similarity is low, there is a possibility that the function is not properly representing the periodic movement of the organ. Therefore, the function has a high possibility that a clutter component that is supposed to be removed is not removed, or a necessary component that is to be kept is removed. Accordingly, the notification function 175 notifies that the similarity is low, that is, that the reliability of a measurement result of a shear wave generated by applying pressure to an organ is low. The notification function 175 may notify by any method. For example, the notification function 175 may notify by displaying on the display 103, may notify by lighting a light emitting diode (LED) or the like, may notify by sound, or may notify by transmitting information to other devices.

The error correcting function 176 corrects an error of a displacement included in the second displacement information in a period in which pressure is applied to an organ based on a function. The error correcting function 176 is one example of a correcting unit. In other words, the error correcting function 176 corrects a discontinuity caused by the push pulse. While the push pulse is irradiated, the ultrasound diagnostic apparatus 100 does not receive a reflection wave of the push pulse. Soon after the tracking period starts after irradiation of the push pulse is finished, the ultrasound diagnostic apparatus 100 receives a reflection wave of the push pulse. Therefore, the error correcting function 176 calculates a displacement of the organ in the period in which the push pulse is transmitted based on a function corresponding to a period cut out by the function applying function 174 in which the push pulse is irradiated. The error correcting function 176 corrects the second displacement information, matching with the calculation result.

Figure 6:
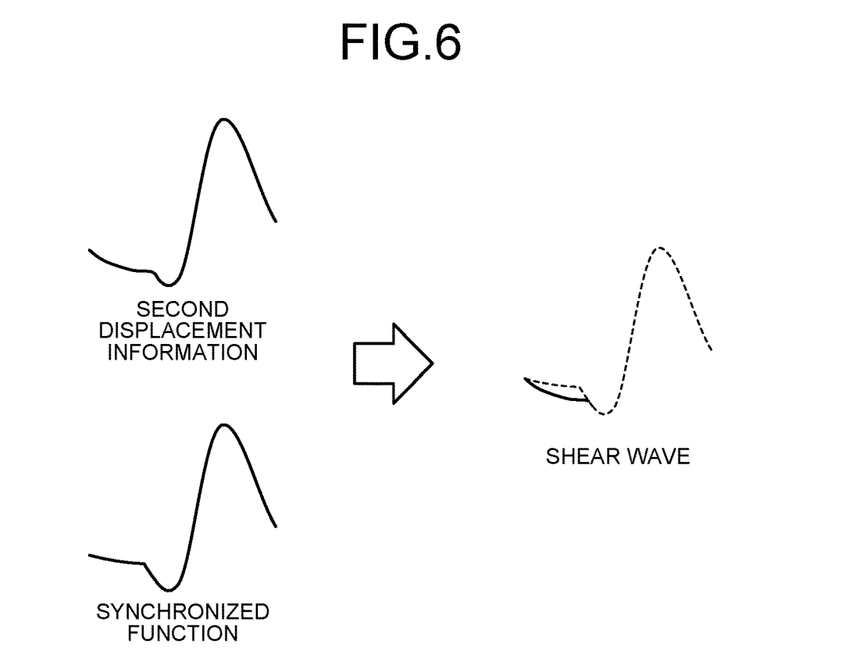
FIG. 6 is an explanatory diagram illustrating an example of a calculation method of shear wave based on second displacement information and a function.

The clutter removing function 177 calculates a shear wave that propagates through an organ by applied pressure, based on a function relating to the clutter component originating from the organ and on the second displacement information relating to a displacement over time of the organ after pressure is applied to the organ. The clutter removing function 177 is one example of a second calculating unit. The second displacement information is one example of second ultrasound information. That is, the clutter removing function 177 calculates a shear wave that propagates through an organ by applied pressure based on the function synchronized by the function applying function 174 and on the second displacement information. FIG. 6 is an explanatory diagram illustrating an example of a calculation method of a shear wave based on the second displacement information and the function. In the shear wave illustrated in FIG. 6, a solid line indicates a shear wave that propagates through an organ by applied pressure, and a doted line indicates a displacement of the organ itself. As illustrated in FIG. 6, the clutter removing function 177 calculates a shear wave by removing the clutter component from the second displacement information based on the function synchronized by the function applying function 174. Thus, the clutter removing function 177 calculates a shear wave that are generated by applying pressure to an organ by the push pulse.

The display control function 178 displays the shear wave that propagates through the organ calculated by the clutter removing function 177 on the display 103. Moreover, the display control function 178 may display hardness of the organ estimated from the shear wave, not just a shear wave. For example, the display control function 178 estimates hardness at respective points of an organ based on a shear wave that propagates through the organ. The display control function 178 then displays an image in which colors according to hardness are superimposed on a B-mode image of the organ including the respective points. Not limited to the display 103, the display control function 178 may display it on a display device that is connected through the NW interface, or may display on other devices.

Next, measurement processing performed by the ultrasound diagnostic apparatus 100 will be explained. The measurement processing is processing of measuring a shear wave that propagates through an organ caused by applying pressure thereto.

Figure 7:
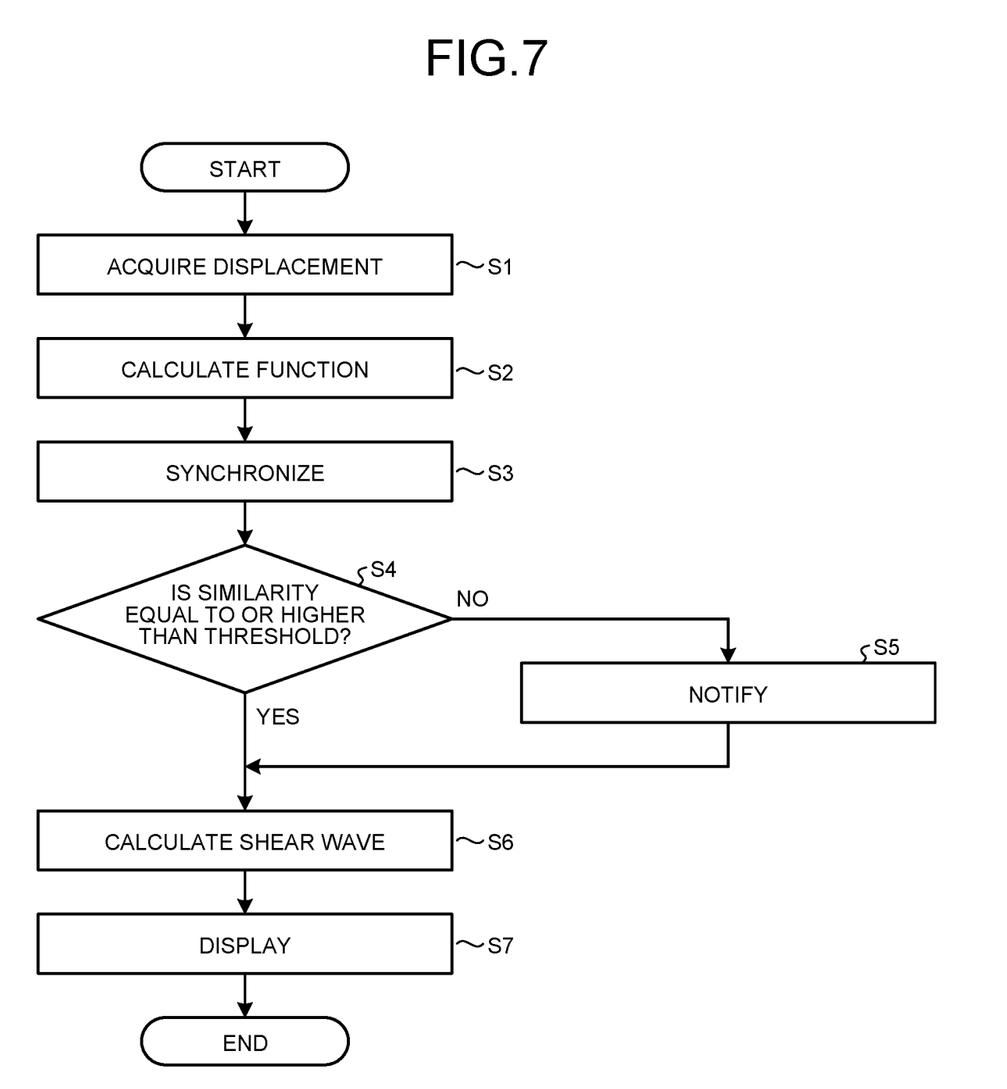
FIG. 7 is a diagram illustrating an example of measurement processing performed by the ultrasound diagnostic apparatus according to the present embodiment.

FIG. 7 is a diagram illustrating an example of measurement processing performed by the ultrasound diagnostic apparatus 100 according to the present embodiment.

The measurement-result acquiring function 172 acquires the first displacement information in which a movement of at least one cycle of an organ that makes a periodic movement is recorded, and the second displacement information in which a displacement indicated by reflection wave data of the tracking pulse repeatedly irradiated is recorded (step S1). The measurement-result acquiring function 172 may acquire the first displacement information and the second displacement information at another timing when performing the measurement processing while irradiating an ultrasonic wave to the subject P.

The movement estimating function 173 calculates a function relating to a clutter component originating from an organ based on the first displacement information relating to a displacement over time of the organ that makes a periodic movement (step S2).

The function applying function 174 synchronizes a clutter component originating from the organ represented by a function and a displacement indicated by reflection wave data of the tracking pulse included in the second displacement information (step S3).

The notification function 175 determines whether the similarity between a waveform of a displacement represented by the function synchronized by the function applying function 174 and a waveform of a displacement indicated by the reflection wave data of the tracking pulse is equal to or higher than a threshold (step S4).

When the similarity is lower than the threshold (step S4: NO), the notification function 175 notifies that the similarity between the waveform of the displacement represented by the function and the waveform of the displacement indicated by the reflection wave data of the tracking pulse is low (step S5).

When the similarity is equal to or higher than the threshold (step S4: YES), the notification function 175 does not notify. Moreover, timing of determination of the similarity or timing of notification are not limited to those at step S5, but may be changed arbitrarily. For example, the notification function 175 may calculate the similarity between a waveform of a displacement represented by a function and a waveform of a displacement indicated by reflection wave data of the tracking pulse after calculation but before synchronization of the function, and may notify according to the calculated similarity. Alternatively, the notification function 175 may calculate respective similarities at multiple timings, and may notify according to the calculated similarities.

The clutter removing function 177 calculates a shear wave that propagates through an organ cause by applying pressure thereto based on a function relating to a clutter component originating from the organ that makes a periodic movement and the second displacement information in which a displacement over time of the organ after pressure is applied to the organ is recorded (step S6).

The display control function 178 displays hardness of respective points of the organ estimated based on the calculated shear wave (step S7).

As above, the ultrasound diagnostic apparatus 100 finishes the measurement processing.

As described above, the ultrasound diagnostic apparatus 100 according to the present embodiment irradiates a reference pulse to an organ that makes a periodic movement, such as heart, irradiates the push pulse to apply pressure to the organ, and irradiates the tracking pulse to the organ after application of pressure. The ultrasound diagnostic apparatus 100 generates the first displacement information relating to a displacement over time of the organ that makes a periodic movement based on Doppler data that is generated from reflection wave of the reference pulse. Moreover, the ultrasound diagnostic apparatus 100 generates the second displacement information relating to a displacement over time of the organ after pressure is applied to the organ based on the Doppler data generated from the reflection wave of the tracking pulse. Moreover, the ultrasound diagnostic apparatus 100 calculates a function relating to a clutter component originating from the organ based on the first displacement information. Furthermore, the ultrasound diagnostic apparatus 100 calculates a shear wave that propagates through the organ by applying pressure thereto based on the calculated function and the second displacement information. In other words, the ultrasound diagnostic apparatus 100 calculates a shear wave that propagates through the organ by applying pressure thereto, by removing a displacement of the organ itself by the function. Therefore, the ultrasound diagnostic apparatus 100 can adopt SWE also to an organ that makes a periodic movement.

First Modification

In the present embodiment, it has been explained that the ultrasound diagnostic apparatus 100 implements the irradiation control function 171, the measurement-result acquiring function 172, the movement estimating function 173, the function applying function 174, the notification function 175, the error correcting function 176, the clutter removing function 177, and the display control function 178 are implemented by executing a program stored in the storage 150. However, the ultrasound diagnostic apparatus 100 may implement some of or all of the irradiation control function 171, the measurement-result acquiring function 172, the movement estimating function 173, the function applying function 174, the notification function 175, the error correcting function 176, the clutter removing function 177, and the display control function 178 by hardware, such as a semiconductor circuit.

Second Modification

In the present embodiment, it has been explained that the measurement-result acquiring function 172, the movement estimating function 173, the function applying function 174, the notification function 175, the error correcting function 176, the clutter removing function 177, and the display control function 178 are included the ultrasound diagnostic apparatus 100. However, these functions may be provided in an analysis device, which is a computer device, such as a server and a workstation. Moreover, for example, the ultrasound diagnostic apparatus 100 transmits reflection wave data stored in the buffer memory 120 to an analysis device through an interface, such as the NW interface circuitry 160. That is, the ultrasound diagnostic apparatus 100 transmits the first displacement information and the second displacement information to the analysis device. The analysis device performs various kinds of processing with respect to the first displacement information and the second displacement information.

According to at least one of the embodiments explained above, SWE can be adopted also to an organ that makes a periodic movement.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnostic apparatus, comprising:
processing circuitry configured to
acquire first ultrasound information relating to a first displacement over time of an organ that makes a periodic movement by repeatedly irradiating the organ with a first ultrasonic wave during a period in which the organ makes the periodic movement at least for one cycle;
irradiate a second ultrasonic wave to apply pressure to the organ;
acquire second ultrasound information relating to a second displacement over time of the organ after the pressure is applied to the organ by repeatedly irradiating the organ with a third ultrasonic wave;
calculate, based on the first ultrasound information, a function relating to the first displacement over time of the organ, and
calculate, based on the function and the second ultrasound information, a shear wave that propagates through the organ by the applied pressure.

2. The ultrasound diagnostic apparatus according to claim 1, wherein the processing circuitry is further configured to calculate the shear wave by removing the first displacement over time of the organ from the second ultrasound information based on the function.

3. The ultrasound diagnostic apparatus according to claim 1, wherein the processing circuitry is further configured to synchronize the first displacement over time of the organ represented by the function and the second displacement over time of the organ indicated by the second ultrasound information, and calculate the shear wave based on the synchronized function and the second ultrasound information.

4. The ultrasound diagnostic apparatus according to claim 3, wherein the processing circuitry is further configured to synchronize the first placement over time of the organ represented by the function and the second displacement over time of the organ indicated by the second ultrasound information based on an electrocardiographic waveform of the organ.

5. The ultrasound diagnostic apparatus according to claim 3, wherein the processing circuitry is further configured to synchronize the first displacement over time represented by the function and the second displacement over time of the organ represented by the second ultrasound information, based on a correlation function to calculate a similarity between the first placement over time of the organ represented by the function and the second displacement over time of the organ indicated by the second ultrasound information.

6. The ultrasound diagnostic apparatus according to claim 1, wherein the processing circuitry is further configured to notify when a similarity that indicates a degree of similarity between the first displacement over time of the organ represented by the function and the second displacement over time of the organ indicated by the second ultrasound information is lower than a threshold.

7. The ultrasound diagnostic apparatus according to claim 1, wherein the processing circuitry is further configured to correct an error in the second displacement in a period in which the pressure is applied to the organ included in the second ultrasound information based on the function.

8. The ultrasound diagnostic apparatus according to claim 1, further comprising an ultrasound probe that irradiates pulsed ultrasonic waves and that receives a reflection wave, wherein the ultrasound probe alternately performs repeated irradiation of a second pulsed ultrasonic wave to apply the pressure to the organ and repeated irradiation of a third pulsed ultrasonic wave to acquire the second ultrasound information, after repeatedly irradiating a first pulsed ultrasonic wave to acquire the first ultrasound information.

9. The ultrasound diagnostic apparatus according to claim 1, wherein the processing circuitry is further configured to estimate a hardness of respective points of the organ based on the shear wave.

10. The ultrasound diagnostic apparatus according to claim 9, wherein the processing circuitry is further configured to display the estimated hardness of the respective points of the organ on a display.

11. An analysis device, comprising:
processing circuitry that is configured to
    acquire first ultrasound information relating to a first displacement over time of an organ that makes a periodic movement by repeatedly irradiating the organ with a first ultrasonic wave during a period in which the organ makes the periodic movement at least for one cycle;
    irradiate a second ultrasonic wave to apply pressure to the organ;
    acquire second ultrasound information relating to a second displacement over time of the organ after the pressure is applied to the organ by repeatedly irradiating the organ with a third ultrasonic wave;
    calculate, based on the first ultrasound information, a function relating to first placement over time of the organ, and
    calculate, based on the function and the second ultrasound information, a shear wave that propagates through the organ by the applied pressure.

12. An analysis method, comprising:
acquiring first ultrasound information relating to a first displacement over time of an organ that makes a periodic movement by repeatedly irradiating the organ with a first ultrasonic wave during a period in which the organ makes the periodic movement at least for one cycle;
irradiating a second ultrasonic wave to apply pressure to the organ;
acquiring second ultrasound information relating to a second displacement over time of the organ after the pressure is applied to the organ by repeatedly irradiating the organ with a third ultrasonic wave;
calculating, based on the first ultrasound information, a function relating to first placement over time of the organ; and
calculating, based on the function and the second ultrasound information, a shear wave that propagates through the organ by the applied pressure.

* * * * *